(12) United States Patent
Suyama

(10) Patent No.: US 6,559,296 B2
(45) Date of Patent: May 6, 2003

(54) DNA CAPILLARY

(75) Inventor: Akira Suyama, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/790,061

(22) Filed: Feb. 21, 2001

(65) Prior Publication Data

US 2002/0013457 A1 Jan. 31, 2002

Related U.S. Application Data

(63) Continuation-in-part of application No. 09/297,035, filed as application No. PCT/JP98/03852 on Aug. 28, 1998, now abandoned.

(30) Foreign Application Priority Data

Aug. 29, 1997 (JP) ............................................. 9-234145

(51) Int. Cl.$^7$ ......................... C07H 21/02; C07H 21/04; G01N 21/05; B29C 65/18; C12Q 1/68
(52) U.S. Cl. ..................... 536/23.1; 436/46; 435/288.5; 422/102; 422/103; 156/503; 156/158; 156/499
(58) Field of Search ........................... 435/6, 46, 288.5, 435/45, 47; 536/22.1; 422/102, 103; 156/503

(56) References Cited

U.S. PATENT DOCUMENTS

| | | | |
|---|---|---|---|
| 5,424,186 A | 6/1995 | Fodor et al. | |
| 5,607,646 A | 3/1997 | Okano et al. | ............... 422/101 |
| 5,688,642 A | 11/1997 | Chrisey et al. | ................. 435/6 |
| 5,855,731 A | * 1/1999 | Spencer | |
| 5,922,604 A | 7/1999 | Stapleton et al. | .............. 435/46 |

FOREIGN PATENT DOCUMENTS

| | | |
|---|---|---|
| EP | 0 430 248 | 6/1991 |
| JP | 7-505529 | 6/1995 |
| JP | 7-506561 | 7/1995 |
| WO | WO 82/02211 | 7/1982 |
| WO | WO 92/04613 | 3/1992 |

OTHER PUBLICATIONS

Woolley et al., "Ultra–High–Speed DNA Sequencing Using Capillary Array Electrophoresis Chips", *Proc. S.P.I.E.*, vol. 2386, pp. 36–44 (1995).

Stephen P.A. Fodor, J. Leighton Read, Micheal C. Pirrung, Lubert Stryer, Amy Tsai Lu, Dennis Solas, *Science, 251*, "Light–Directed, Spatially Addressable Parallel Chemical Synthesis", pp. 767–773, Feb. 15, 1991.

Woolley et al., "Ultra–high–speed DNA Fragment Separations Using Microfabricated Capillary Array Electrophoresis Chips", *Proc. Natl. Acad. Sci. USA, 91*, pp. 11348–11352 (1994).

* cited by examiner

*Primary Examiner*—W. Gary Jones
*Assistant Examiner*—Arun K. Chakrabarti
(74) *Attorney, Agent, or Firm*—Frishauf, Holtz, Goodman & Chick, P.C.

(57) ABSTRACT

The present invention relates to an apparatus for detecting nucleic acid molecules such as target DNA molecules and mRNA molecules by using a DNA probe, and provides a DNA capillary, comprising a fluid passageway formed of a cylindrical capillary made of glass, a plurality of independent probe regions formed in the inner wall of the fluid passageway, and DNA probes each immobilized in the probe region, the immobilized DNA probes differing from each other. For performing the measurement, a sample is introduced through an open portion into the capillary so as to perform reaction and, then, fluorimetry.

27 Claims, 7 Drawing Sheets

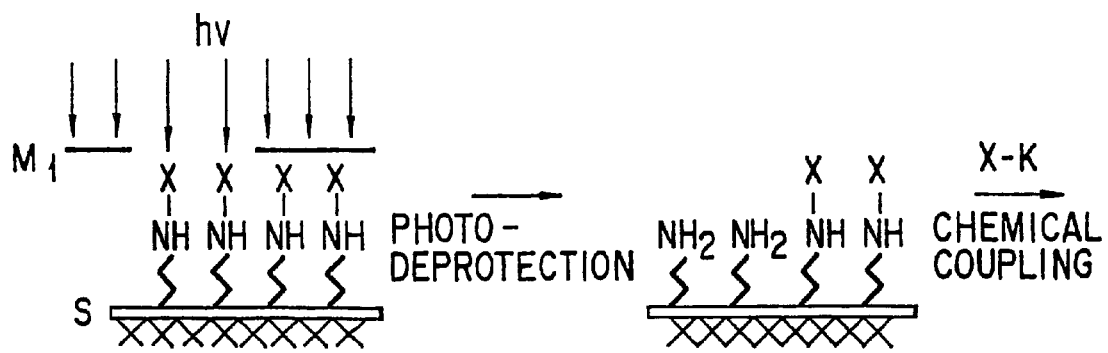
FIG. 1A
PRIOR ART
FIG. 1B
PRIOR ART
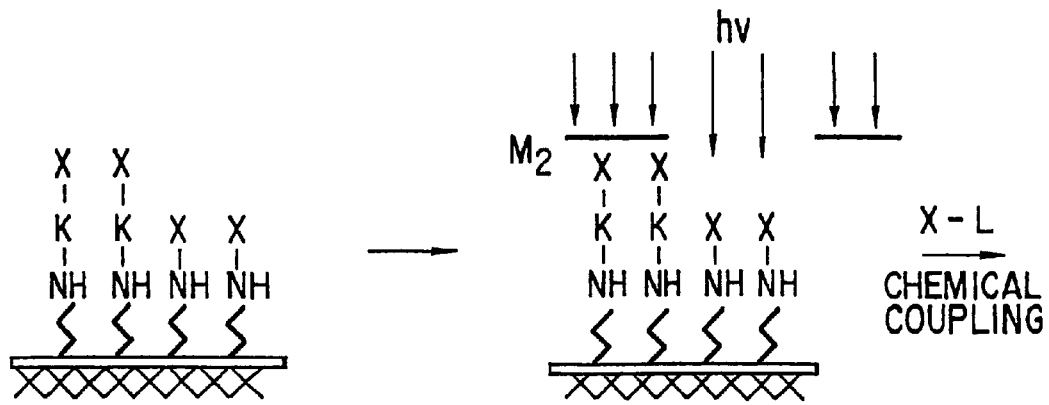
FIG. 1C
PRIOR ART
FIG. 1D
PRIOR ART
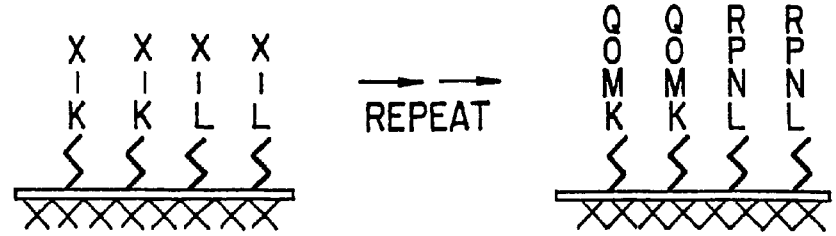
FIG. 1E
PRIOR ART
FIG. 1F
PRIOR ART

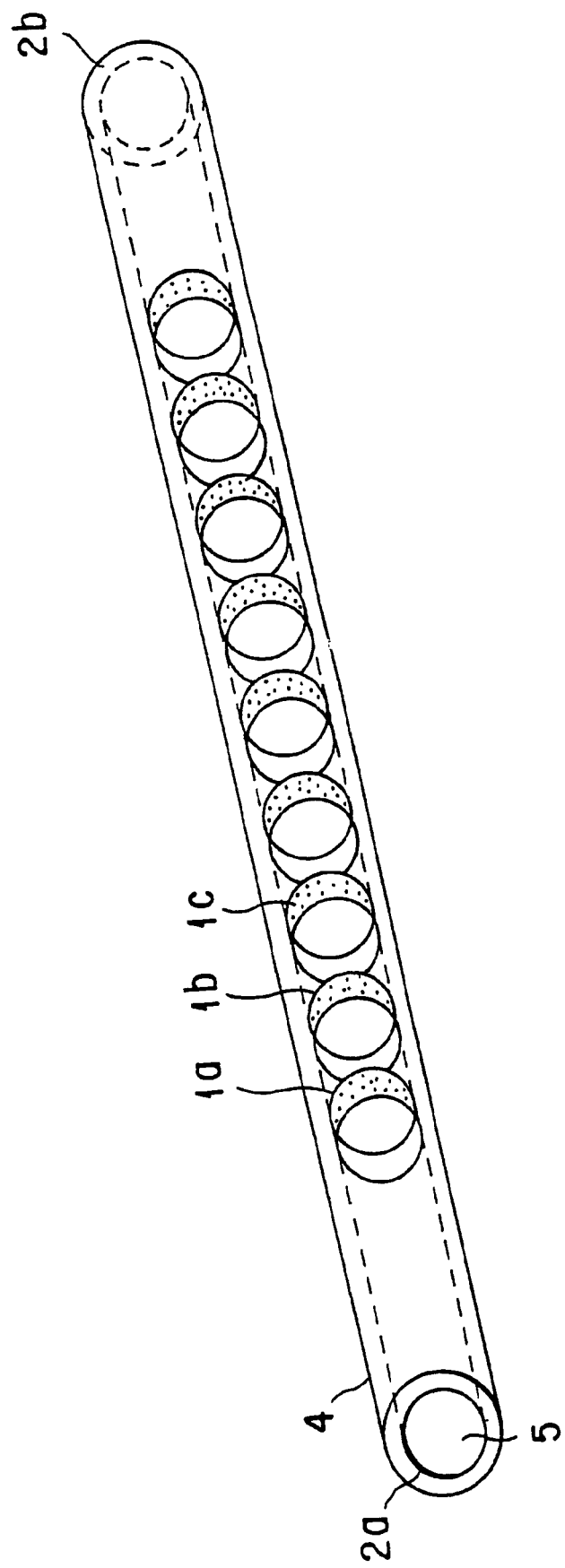
F I G. 2

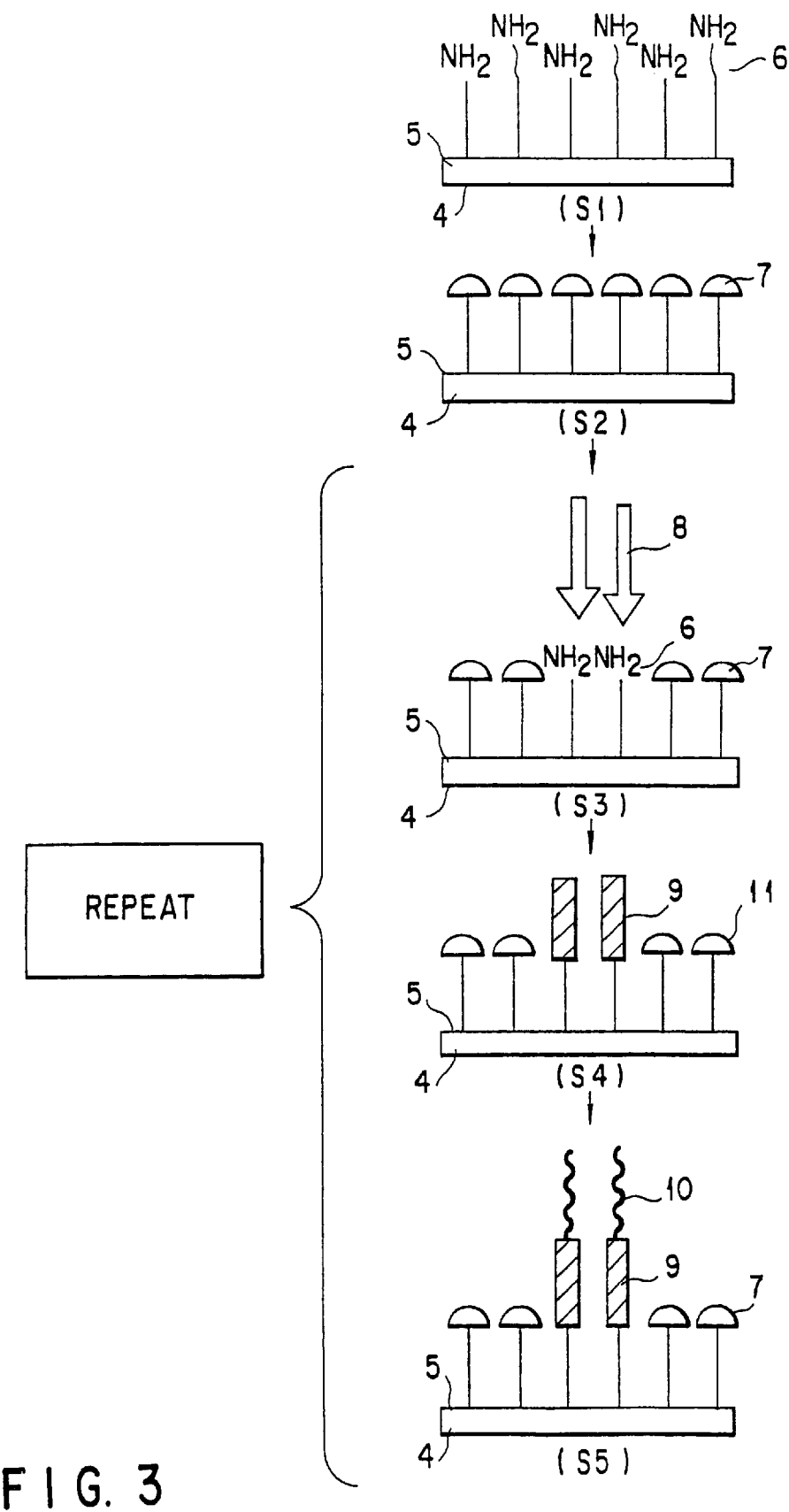
F I G. 3

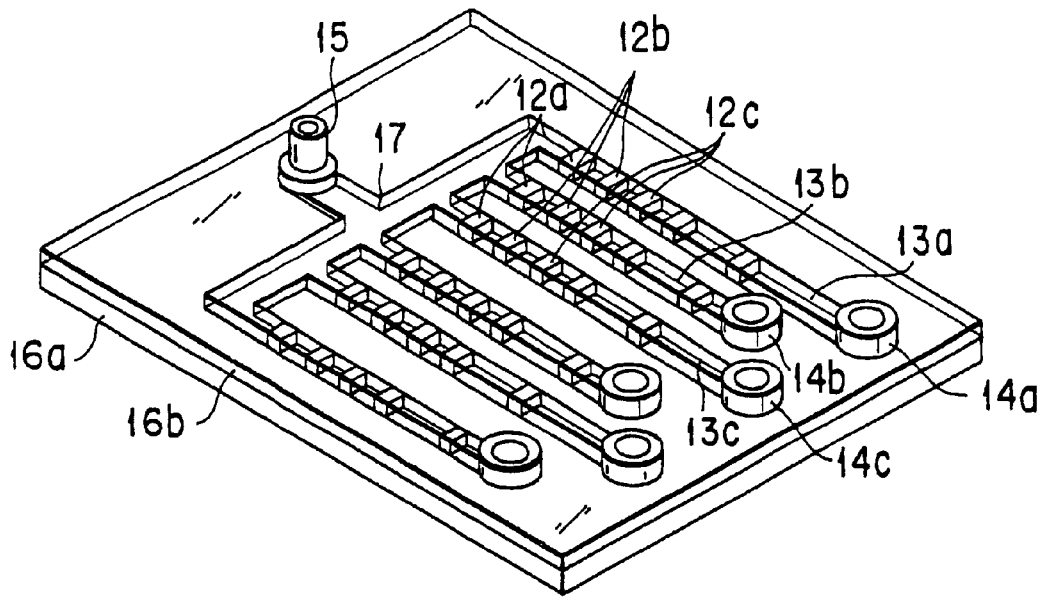
F I G. 4A
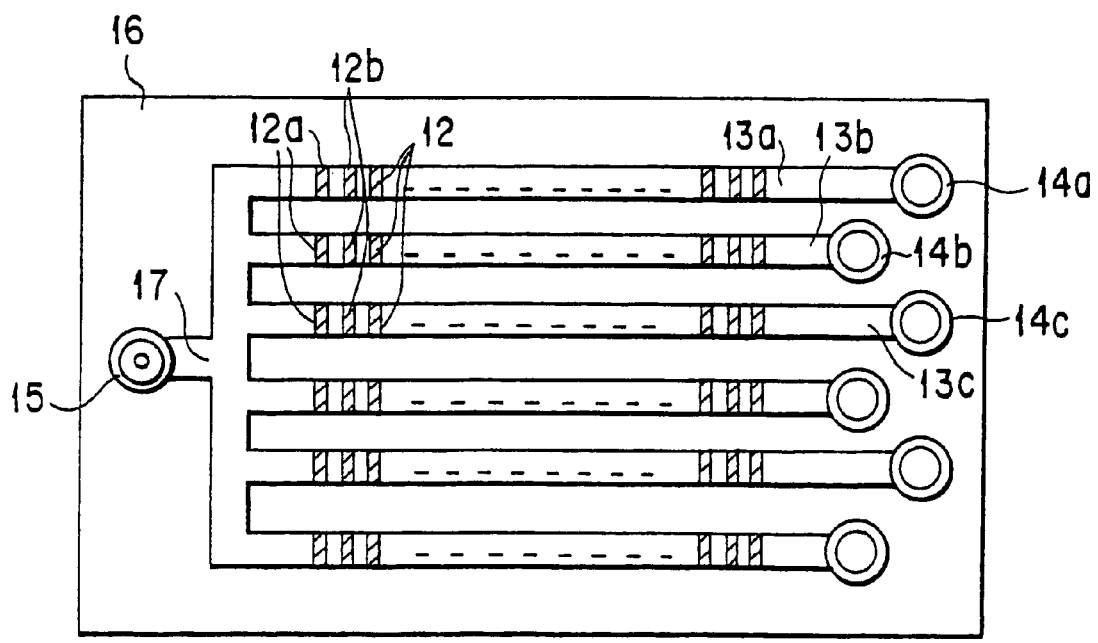
F I G. 4B

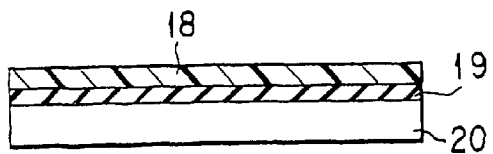
FIG. 5A
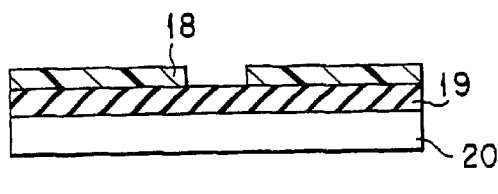
FIG. 5B
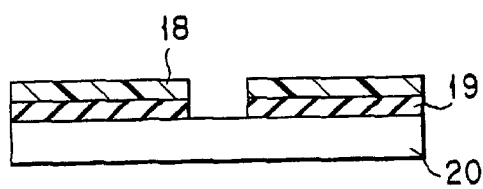
FIG. 5C
FIG. 5D
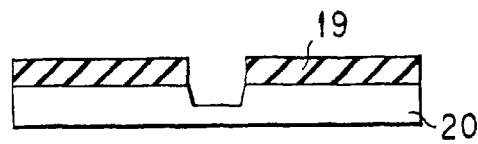
FIG. 5E
FIG. 5F
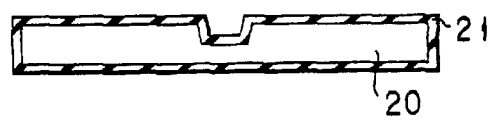
FIG. 5G
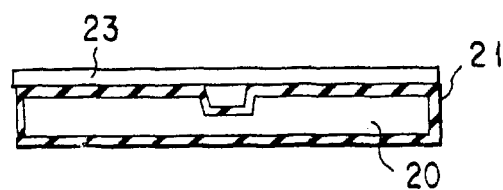
FIG. 5H F I G. 6A
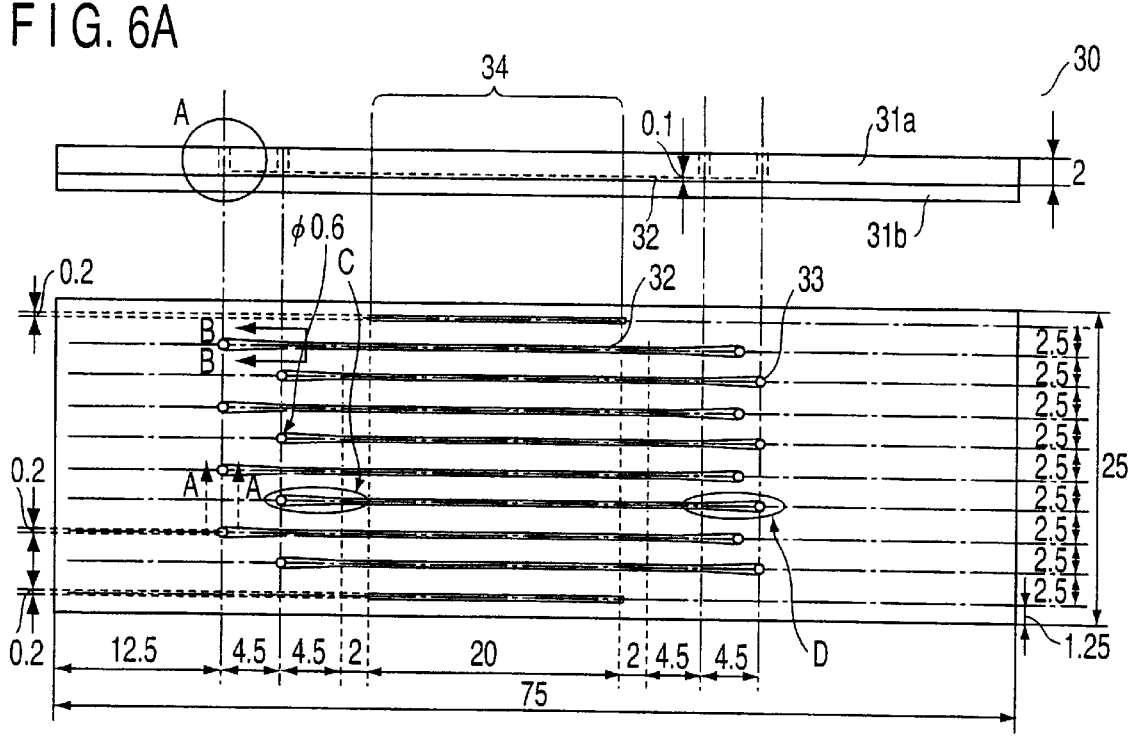
F I G. 6B
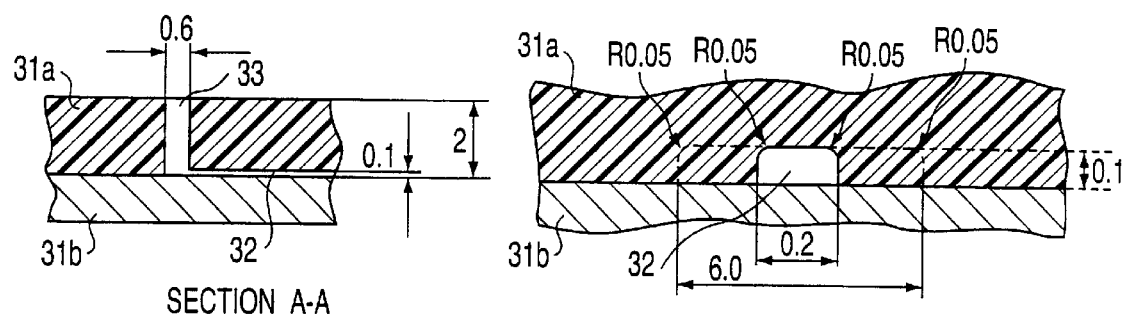
SECTION A-A
SCALE – 5:1
F I G. 6C
SECTION B-B
SCALE – 50:1
F I G. 6D
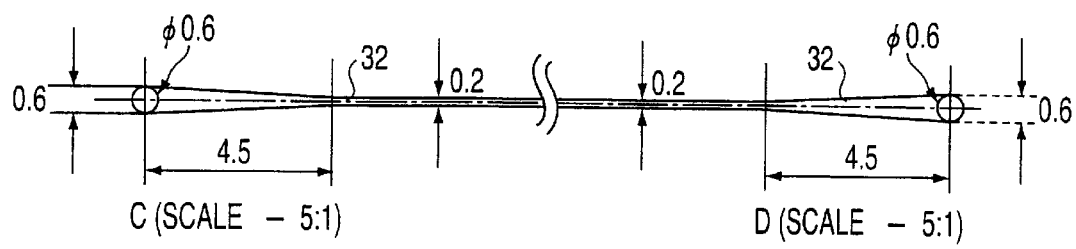
C (SCALE – 5:1)    D (SCALE – 5:1)
F I G. 6E

DNA CAPILLARY

CROSS REFERENCE TO RELATED APPLICATIONS

This is a Continuation-in-Part Application of Application No. 09/297,035, filed Apr. 26, 1999, which in turn is based on PCT Application No. PCT/JP98/03852, filed Aug. 28, 1998, the said PCT Application having not been published under PCT Article 21(2) in English. The entire contents of both of the above applications Ser. Nos. 09/297,035 and PCT/JP98/03852 are incorporated herein by reference.

This application is based upon and claims the benefit of priority from the prior Japanese Patent Application No. 09-234145, filed Aug. 29, 1997.

BACKGROUND OF THE INVENTION

The present invention relates to an apparatus for detecting a target DNA, a target mRNA, etc. by using a DNA probe.

In recent years, a human genome project, i.e., an attempt to analyze the base sequence in all the human genes, is being carried out worldwide. The human genome analysis including the determination of the base sequence is a very complex and laborious work. It is said, however, that the human genome project will be completed at the beginning of the 21st century. Development of many novel technologies as well as improvement and automation of the analytical equipment greatly contributes to the promotion of the human genome project. A DNA chip technology is one of the newly developed analytical technologies.

The DNA chip is a chip prepared by spotting many kinds of DNA probes at predetermined positions on a substrate, e.g., a silicon wafer, by utilizing the lithographic technology used in the field of semiconductor devices. The DNA probe is formed of an oligonucleotide having a predetermined sequence of 4 kinds of bases constituting DNA, i.e., adenine (A), guanine (G), cytosine (C) and thymine (T). The sequence is complementary to the base sequence of the target DNA or mRNA. For example, if the sequence of AGCTT (5'→3') is used as a DNA probe, a DNA having a base sequence of AAGCT, which is complementary to the sequence of AGCTT noted above, is hybridized with the DNA probe so as to be selectively caught. Incidentally, the actual constituting unit of the DNA probe is nucleotide having the above-noted base portion (base portion+ deoxyribose portion+phosphoric acid ester portion). For simplifying the description, however, nucleotide is represented by the base alone in the following description.

A method of immobilizing a DNA probe on the substrate is exemplified in, for example, "Science 251:767–773" published in February 1991. In this method, a DNA probe is formed on a flat substrate by utilizing a photochemical reaction. Let us describe briefly how to form a DNA probe having a 4-base length on a silicon substrate by this method with reference to FIGS. 1A to 1F.

In the first step, an amino group is formed on a silicon substrate S by treatment with silane, followed by allowing a photo-protective group X to be coupled with each amino group. Then, a desired position is selectively irradiated with an ultraviolet light by using a first mask $M_1$. As a result, a protective group X at a desired position is removed so as to expose the amino group, as shown in FIG. 1A. Then, an optional DNA base (shown by K here) accompanied by the photolabile protecting group is reacted with the exposed amino group, as shown in FIG. 1B. As a result, a portion in which the base K accompanied by the photolabile protecting group X is coupled with the amino group and another portion in which the photolabile protecting group X alone is coupled with the amino group are formed on the substrate, as shown in FIG. 1C. Further, the portion in which the photolabile protecting group X alone is coupled with the amino group is selectively irradiated with light through a second mask $M_2$ so as to selectively remove the photolabile protecting group X in the irradiated portion. Then, an optional DNA base (shown by L here) accompanied by the photolabile protecting group X is coupled with the exposed amino group, as shown in FIG. 1D. As a result, bases K and L accompanied by the photolabile protecting group X are immobilized to the substrate surface with an amino group (not shown) interposed therebetween, as shown in FIG. 1E. Further, similar operations are performed by using an optional DNA base (shown by M here) and another optional DNA base (shown by N here). As a result, a DNA probe having a length of two bases is immobilized to the substrate surface. Still further, similar operations are repeated to stack bases in a three dimensional direction so as to form DNA probes each having a length of four bases, said DNA probes having different base sequences depending on the process units, as shown in FIG. 1F. For forming a base sequence having a length of, for example, eight bases, photolithography using 32 masks and the photoreaction are repeated 32 times so as to form DNA probes having all the desired base sequences. It is theoretically possible to form efficiently DNA probes each having an optional base length and an optional base sequence on a single substrate by utilizing the above-described technology.

An improved method of manufacturing a DNA chip is disclosed in International Laid-open Application WO 93/096668 (Japanese translation version No. 7-506561). In this method, a DNA probe is immobilized on a silicon substrate having an amino group formed thereon by using a flow type channel block. The flow type channel block used in this method is a pattern plate having a plurality of slender channels. In the case of using the pattern plate, it is possible to immobilize the DNA probe along each of these channels. In this case, the base sequence of the DNA probe differs depending on the channel. However, the base sequence is the same over the entire length in a single channel. In this preferred mode of the conventional technology, an amino group is attached first to the substrate, followed by combining the substrate with a block having a plurality of channels arranged in parallel. Then, a process solution containing a base, which is a constituting unit of the selected DNA probe, is allowed to flow through a predetermined channel so as to immobilize the first base of the aimed DNA probe. Further, the substrate and the channel block are rotated relative to each other by a predetermined angle, e.g., 90°, followed by combining again the substrate and the channel block and subsequently immobilizing a base corresponding to the second base along the channel. A DNA probe having a desired base sequence can be prepared by successively repeating the above-noted steps. Also, a large number of DNA chips referred to previously can be manufactured in a single operation by combining the method described above with the photochemical reaction. It should also be noted that screening can be performed by using the DNA chip prepared by the above-noted method in combination with the channel block described above.

In order to prepare the conventional DNA chip, it is necessary to carry out mutual reactions among a large number of reagents on a flat substrate in immobilizing the probe. Also, when the DNA chip is used for measurement, it is necessary to apply many times a liquid material to a surface of a flat DNA chip in order to carry out reactions with a sample and to wash the DNA chip surface. In order to apply the above treatment to a flat substrate (or DNA chip), the substrate (or the DNA chip) must be dipped in a reactant solution filling a container. Alternatively, a flow path must be formed on the DNA chip surface by using an additional tool such as the channel block noted above, followed by applying the treatment with the liquid. However, the dipping method gives rise to a problem that each kind of the treating liquid must be used in an excessive amount in the immobilizing step and in the sample measuring step. On the other hand, in the method using a flow path, only a limited region of the surface of the DNA chip having a DNA probe immobilized thereon is used, resulting in failure to utilize sufficiently the formed DNA chip. Further, the DNA chip is an open system in which the probe-formed surface is exposed to the outside, giving rise to the defects that the surface tends to be contaminated and that the DNA chip cannot be handled conveniently.

The conventional DNA chip technology gives rise to an additional problem besides the problems given above. Specifically, the conventional DNA chip technology is certainly effective for performing the sequencing of DNA having an unknown base sequence, but is not adapted for the developed pattern analysis of mRNA which will be important in the future. Let us describe the particular problem in the following.

In recent researches on genes, how to utilize the DNA information obtained by the sequencing is more important in view of the post genome than the sequencing itself. For example, the analysis of the mRNA expression pattern is being carried out vigorously in order to make researches on the gene expression profile. The expression of mRNA relating to a certain gene exhibits a different level of expression depending on each organ. Even in the same cell line, the level of expression differs depending on phase factors, particular disease factors, etc. The analysis of the difference in the level of the mRNA expression in an individual, i.e., analysis of the expression pattern, can be applied in various technical fields such as gene diagnosis, gene therapy, development of medicines and agricultural and stock raising industries and, thus, a further progress is expected.

In general, a quantitative analysis of mRNA relating to a target gene is required for the analysis of the expression pattern of mRNA. Employed for the quantitative analysis is a method in which mRNA to be measured or cDNA thereof, which is obtained by a reverse transcription from mRNA, is reacted with a DNA probe having a base sequence complementary thereto so as to hybridize both of them and, thus, to achieve detection. In such a research, a plurality of expression levels of mRNA are measured. Therefore, used are a plurality of DNA probes corresponding to these plural target mRNA molecules. It should also be noted that, in a research on the expression pattern of mRNA, the base sequence of the mRNA or cDNA to be measured is known to some extent, making it possible to use a relatively long DNA probe having about 20 to 60 bases, preferably, about 40 bases, in view of the accuracy and efficiency of the measurement. As a matter of fact, such a relatively long DNA probe is actually used. In order to prepare a probe having such a length by the conventional DNA chip technology, a tremendous labor is required such that it is necessary to prepare 80 to 240 masks and to repeat the base synthesis by lithography and photoreaction 80 to 240 times. Further, in order to improve the measuring accuracy, it is necessary to align the length of the DNA probe. In the case of employing the conventional method, it is substantially impossible to synthesize a DNA probe having an aligned base length directly on a substrate in view of the yield of synthesis in each stage.

On the other hand, about 20,000 to 30,000 kinds of genes of about 100,000 genes present in a single cell are considered to express mRNA. Since a ratio of cell specific genes that are important in the research of the expression pattern is estimated at about several percent (about 1 to 3%), about several hundred to thousand of mRNA or their cDNA are considered to be capable of providing a target object to be measured. According to the conventional DNA chip technology described previously, $4^8$ kinds, i.e., 65,536 kinds, of probes each having a length of 8 bases can be formed on a single substrate. However, since a maximum of about 20,000 to 30,000 kinds of mRNA, actually not larger than $1/10$ thereof, are considered to be capable of providing the target object, such a tremendous number of kinds of probes need not be formed in practice.

Further, the hybridization condition between a DNA probe and a target object of an mRNA (or its cDNA) segment is not uniform and requires the stringency in the reaction. In addition, it is impossible in view of the dynamic range of the measuring apparatus to process in a single operation a test sample containing a tremendous number of kinds of target mRNA (or cDNA) pieces widely different from each other in concentration to detect the target mRNA. Therefore, even if a tremendous number of kinds of DNA probes are prepared under the same measuring conditions, only a very small proportion of the DNA probes produce a useful result. Such being the situation, a tremendous number of kinds of DNA probes need not be formed on the same substrate.

Further in the conventional DNA chip technology described previously, the synthesis by photoreaction must be repeated for forming the DNA probe, with the result that deterioration of the DNA probe caused by ultraviolet light remains as a problem to be solved. It follows that the conventional DNA chip technology is unsuitable for use in preparation of a DNA probe having a length of 20 bases or more.

Known vessels and methods are also disclosed in several publications. For example, U.S. Pat. No. 5,607,646 discloses a plate capable of pooling a liquid and having a plurality of DNA probes immobilized on a flat bottom. Also, U.S. Pat. No. 5,922,604 discloses a closed vessel, which is circular and has a flat working area. The inflow and outflow of a sample or the like into and out of the working area are performed in the prior art by utilizing the capillary phenomenon. The working area is formed such that the capillary phenomenon is intensified toward the inner region of the working area. Further, a method of detecting DNA by a capillary electrophoresis is disclosed in "Proc. Natl. Acad. Sci. USA, Vol. 91, pp 11348–11352. In this method, there is no immobilized phase of the probe in the fluid passageway. Also, since the detecting apparatus is immobilized in a predetermined position, the detection is performed at the same site. It follows that this apparatus simply permits detecting the size of the molecule separated by the electrophoresis, and the detection is performed only when the separated molecule passes through the detecting point. However, the methods and the vessels disclosed in these publications are incapable of resolving the problems described above.

BRIEF SUMMARY OF THE INVENTION

A first object of the present invention is to carry out the reaction and/or detection of a plurality of target DNA's at a time promptly under predetermined conditions. And the detection can be performed easily.

A second object of the present invention is to provide a DNA probe apparatus strong against contamination, easy to handle and excellent in efficiency.

A third object of the present invention is to provide a DNA probe apparatus which permits immobilizing the DNA probe without requiring excessive amounts of various processing liquids and also permits enlarging the area that can be utilized.

Further, a fourth object of the present invention is to provide a DNA capillary adapted for analysis of the expression pattern of mRNA.

The first to fourth objects can be achieved by a DNA capillary, comprising a fluid passageway having at least a part thereof defined by a wall capable of transmitting light, a plurality of independent probe regions formed in the inner wall of the fluid passageway, and DNA probes immobilized on the probe regions, respectively, the DNA probes differing from each other depending on the probe regions on which the DNA probes are immobilized.

In an aspect of the present invention, the fluid passageway should desirably be a hollow capillary having the end portion left open. More desirably, the fluid passageway should be a cylindrical capillary. Where the fluid passageway is in the form of a cylinder having the end portion alone left open, the DNA capillary forms a closed system, making it possible to provide a DNA capillary very strong against contamination and easy to handle.

In another aspect of the present invention, a plurality of fluid passageways are arranged in an integral form so as to improve the immobilizing treatment of the DNA probe and the processing capability of the test sample. Particularly, where all of the plural fluid passageways are combined to communicate with each other in the vicinity of at least one end portion of the fluid passageway, the various processing liquids can be collectively introduced into or recovered from the plural fluid passageways through the combined portion.

In another aspect of the present invention, it is desirable to arrange the plural probe regions within a single fluid passageway in the form of annular regions apart from each other along the fluid passageway. The particular arrangement permits improving the efficiency because a plurality of different DNA probes are allowed to perform the detecting function simultaneously by simply passing liquid to be treated, which contains a test sample, or a gas for the drying purpose, through the single fluid passageway only once. Further, in the DNA capillary of the present invention, it is desirable for the different DNA probes to be arranged in annular regions formed over the entire circumferential region of the inner wall of the capillary and positioned apart from each other. The particular construction makes it possible to enlarge the area to be utilized, compared with the conventional DNA chip utilizing a flat plane. As a result, the target substance can be caught efficiently even in the case of using a small amount of a test sample.

In the DNA capillary of the present invention, the fluid passageway can be formed by applying an etching to a glass or silicon substrate. The etching method is useful when a large number of capillaries are prepared by a single processing. In addition, a large number of DNA probes can be immobilized within a large number of capillaries by utilizing a photochemical reaction.

In another aspect of the present invention, it is possible to manufacture a capillary of the present invention from a plastic material by an injection molding. Use of a plastic material permits suppressing the material cost, the processing cost, etc. Also, the method of immobilizing DNA probes employed in the present invention is not limited to a immobilization by photochemical reaction. Specifically, it is also possible to immobilize the DNA probes in the present invention by the conventional spotting method, e.g., a spotting using an ink jet printer.

What should also be noted is that it is desirable in the present invention to use a DNA probe synthesized in advance with a predetermined base sequence and length. In this case, it is possible to provide a DNA probe adapted for the analysis of the expression pattern of mRNA so as to achieve the fourth object of the present invention. To be more specific, since the probe can be immobilized by applying a photochemical reaction only once, it is possible to immobilize stably a DNA probe having at least 20 bases. It follows that it is possible to provide a detecting apparatus adapted for the research on the mRNA expression pattern, though it was impossible to achieve such a detecting apparatus by utilizing the conventional DNA chip technology.

According to another aspect of the present invention, it is possible to immobilize a plurality of kinds of DNA probes to the fluid passageway noted above in a predetermined amount for each kind and independently of each other depending on the kind. It should be noted that the fluid passageway of the DNA capillary according to the present invention has a predetermined constant cross sectional area over at least the processing region. The "processing region" represents the region in which a desired processing is applied to the fluid and denotes at least the region between adjacent probe regions. By making constant the cross sectional area of the processing region, it is possible to fluidize the sample to be processed under the same conditions. The fluid passageway in the present invention is tubular. One probe region is arranged circular on the inner wall in a manner to make one complete rotation around the periphery of the fluid contained in the capillary, thereby detecting a desired nucleic acid with a high sensitivity and smoothly.

According to still another aspect of the present invention, it is possible for the cross sectional shape of the fluid passageway to be bent at least partially. To be more specific, it is possible for the cross section of the capillary to be elliptical, circular, arcuate, rectangular, rectangular with one or more roundish corners, or to have a cross sectional shape obtained by combination of these cross sectional shapes. Such shapes are effective for preventing the bubbles from staying in the fluid passageway. Particularly, the shape defined above is effective for preventing the bubble generation and growth under high temperature conditions employed in the DNA reaction, e.g., high temperature equal to the melting point. It is desirable for the cross section of the fluid passageway to be shaped rectangular with roundish corners because the capillary can be manufactured easily and the bubble formation can be prevented.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 1A to 1F schematically show a conventional method of immobilizing DNA probes.

FIG. 2 shows a DNA capillary according to a first embodiment of the present invention.

FIG. 3 schematically shows a method of immobilizing DNA probes on the inner wall of a capillary.

FIGS. 4A and 4B collectively show a DNA capillary with integrated passageways according to a second embodiment of the present invention, wherein FIG. 4A is an oblique view, and FIG. 4B is a plan view.

FIGS. 5A to 5H are cross sectional views collectively showing how to form a groove by utilizing a semiconductor processing technology for a DNA capillary of the present invention.

FIGS. 6A to 6E collectively show a DNA capillary array having DNA probes on the bottom of the fluid passageway of the capillary according to a third embodiment of the present invention, wherein FIG. 6A is a side elevation view, FIG. 6B is a plan view, FIG. 6C and 6D are cross sectional views along the A—A and B—B, respectively, shown in FIG. 6B, and FIG. 6E is a plan view showing in a magnified fashion some regions shown in FIG. 6B.

DETAILED DESCRIPTION OF THE INVENTION

EXAMPLE 1

Figure 7:
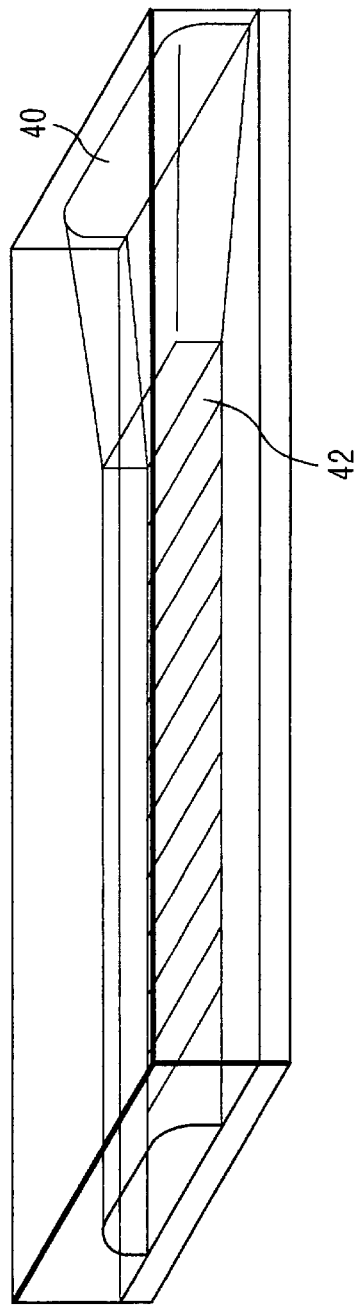
FIG. 7 shows a DNA capillary according to a modification of Example 4.

FIG. 2 shows a DNA capillary according to a first embodiment of the present invention. As shown in the drawing, DNA probes 1a, 1b, 1c, etc. differing from each other in kind are immobilized in annular probe regions formed separately from each other on an inner wall 5 of a cylindrical capillary 4 having an injecting open end portion 2a and a discharging open end portion 2b and made of a light transmitting material. It is possible to use the capillary 4 having an inner diameter of about 0.1 mm to about 5 mm. However, the inner diameter of the capillary 4 should desirably be about 0.5 mm to 1 mm to make the capillary 4 easy to handle. The length of the fluid passageway of the capillary 4 should desirably be about 5 mm to about 100 mm. It suffices to determine the inner diameter and the length of the fluid passageway of the capillary 4 depending on the amount of the sample to be measured and the fluidity of the liquid.

The probe immobilized within the capillary 4 consists of a desired base sequence synthesized in advance and should desirably consist of at least 20 bases, preferably 20 to 60 bases, particularly about 40 bases (e.g., 35 to 45 bases). The total number of kinds of the probes immobilized to a single capillary, which differs depending on the object, depends on the number of mRNA molecules to be measured or cDNA molecules converted from the mRNA molecules in a single sample. The number of objects to be measured in the present invention, which are contained in a single sample, ranges from one kind to thousands of kinds. For analyzing the expression pattern of mRNA, which is an object of the present invention, it is necessary to immobilize thousands of kinds of DNA probes. On the other hand, for inspecting, for example, an infectious disease, it suffices to immobilize one to several kinds of DNA probes.

The distance between adjacent DNA probes, e.g., between DNA probes 1a and 1b, should be small where many objects are to be inspected. By contraries, where the number of objects to be measured is small, the distance between adjacent DNA probes can be enlarged. In fact, where a plurality of kinds of DNA probes each having about 20 to 60 bases are arranged for each kind in annular probe regions separated from each other, the DNA probes 1a, 1b, 1c, etc. can be arranged about 1 μm to 5 mm apart from each other. It is also possible to immobilize a plurality of DNA probes of the same kind or to immobilize one or more reference proteins, as desired, leading to an increased diversity of the measurement. In view of the case where traces of object is measured, it is generally desirable to employ a photosensitizing system utilizing fluorescent emission or chemical luminescent emission for the measurement using a DNA capillary. Where the DNA probes 1a, 1b, 1c, etc. are immobilized very close to each other in the capillary 4, it is necessary to read individually a plurality of reaction patterns by using a measuring means having a high resolution such as a fluorescence microscope. On the other hand, where the DNA probes are arranged a large distance, i.e., several millimeters, apart from each other, a naked eye observation can be performed by using a transilluminator. For facilitating the light measurement and observation, it is desirable to use a DNA capillary formed of an optional material excellent in its capability of transmitting light such as plastic materials, silica, glass, polymer or the like. Particularly, it is desirable to use glass or silicon in employing a manufacturing method involving a treatment with silane, which is a step for immobilizing a DNA probe and will be described herein later. If necessary, the DNA capillary may partially reflect or shield light. It is advantageous to use a glass capillary available on the market because the DNA capillary can be manufactured at a low cost. Also, in the case of using a capillary made of a plastic material, it is desirable to use a plastic material having an OH group acting as a means for coupling a DNA probe. In this case, a silane treating agent can be used. However, the plastic material used is not limited to the particular material. Any type of a plastic material can be used as far as the plastic material has a means for coupling a DNA probe.

The manufacturing method of a DNA capillary will now be described. FIG. 3 shows how various DNA probes 1a, 1b, 1c, etc. are immobilized on the inner wall 5 of the glass capillary 4. The application of various processing liquids in each manufacturing process can be performed by introduction of the processing liquid through the injecting open end portion 2a of the capillary by a suitable dispensing means and by discharge of the processing liquid through the discharging open end portion 2b by a suitable suction means in the after-treatment. A discharge means such as pipetting and other suitable means can be used as the dispensing means. Also, any type of suction means can be used. It is also possible to employ a natural injection and natural discharge by capillary action.

The manufacturing method will now be described with reference to the scheme shown in FIG. 3. In the first step, a solution containing a silane coupling agent for the silane treatment is applied to the capillary 4 so as to form amino groups ($NH_2$) on the inner wall 5 (step S1). Then, a solution containing a capping agent 7 which is subjected to photodecomposition upon irradiation with light having a predetermined wavelength, preferably ultraviolet light, is applied to the capillary 4 to allow the capping agent 7 to be coupled with all the amino groups on the surface of the inner wall 5 (step S2). In the next step, the regions in which DNA probes 10 are to be immobilized are selectively irradiated with an ultraviolet light 8 so as to decompose the capping agent 7 and, thus, to expose the amino groups (step S3). The lithography technology employed in the field of semiconductor can be employed for selectively irradiating the desired regions with the ultraviolet light 8. To be more specific, a mask member is used for selectively shielding the ultraviolet light. Alternatively, a lens system can be used for narrowing the range of light irradiation. Since the capillary 4 is cylindrical, the light irradiation can be performed in an optional direction as far as the irradiating light is incident at an angle substantially perpendicular to the side surface of the capillary. Further, since light can be transmitted through the entire region of the capillary 4, the inner wall 5 is deprotected in an annular shape in the region irradiated with the ultraviolet light.

Then, a liquid containing a linker molecule 9 is applied to the capillary 4 (step S4). The linker molecule 9, which is interposed between the amino group 6 bound to the inner wall 5 and the DNA probe 10 so as to link the amino group 6 to the DNA probe 10, has at one end a coupling portion reacting with the amino group to form a bond and at the other end another coupling portion reacting with the amino group or a thiol group to form a bond. The linker molecule 9 applied to the capillary 4 is coupled with the amino group 6 by the coupling portion at one end (step S4). In this step, the coupling portion at the other end is rendered free. Then, a liquid containing the DNA probe 10 having an amino group or thiol group formed at the terminal portion is introduced so as to permit the DNA probe 10 to be coupled with the linker molecule 9 (step S5).

Incidentally, the immobilizing process in each of steps S3, S4 and S5 can be performed while employing a process of washing the inner space of the capillary 4 by using a suitable amount of a washing liquid. Further, a DNA capillary as shown in FIG. 2, i.e., a DNA capillary in which the aimed DNA probes 1a, 1b, 1c, etc. are independently immobilized in the shape of a ring in aimed positions, can be prepared by repeating the above process in another position a desired distance apart from the original position. The term "ring-like" or "annular" shape used herein denotes various shapes such as circular, polygonal and elliptical shapes corresponding to the cross sectional shape of the hollow capillary 4 forming the fluid passageway. Also, the term "fluid passageway" used herein denotes a passageway having a width and a height large enough to allow at least a required amount of the processing liquid to flow therethrough. Preferably, the fluid passageway is selected to be capable of obtaining the flow promoting function by the capillary action. It follows that a surface simply having concave-convex configurations formed thereon is not called the fluid passageway. That is to say, DNA capillary of the present invention is not formed of a surface that is simply irregular.

The silane coupling agent used in step S1 includes, for example, aminoethyl-aminopropyl-trimethoxy-silane, though other compounds can also be used as the silane coupling agent as far as amino groups can be formed on the surface. For example, it is also possible to use amino silanes such as aminoethyl-aminopropyl-methyl dimethoxy-silane.

The capping agent used in step S2 includes, for example, 4,5-Dimethoxy-2-nitrobenzyl chloroformate, 6-Nitroveratryl chloroformate, 4-Nitrobenzyl chloroformate, and o-Nitrobenzyl-p-nitrophenyl carbonate. However, the capping agent is not limited to these compounds. It is possible to use any substance as the capping agent as far as the substance exhibits an intramolecular cleavage such that the coupling with the amino group can be released upon irradiation with an ultraviolet light or a visible light.

Light having a wavelength of about 350 nm is generally used in step S3. However, light having a wavelength adapted for obtaining an optimum photodecomposition can be selected depending on the kinds of the capping agent and the solvent used. Also, an optical apparatus available on the market can be used for irradiation of a specified light such as an ultraviolet light.

The linker molecule 9 used in step S4 includes, for example, homobifunctional N-hydroxysuccinimidyl (NHS) esters such as Disuccinimidyl suberate and homo-bifunctional imidoesters such as Dimethyladipimidate-2-HCL. The linker molecule used in Example 1 has succinimide groups reacting with the amino group at both terminals of the molecule. However, it is possible for the functional groups at both terminals to differ from each other. For example, it is possible to use a linker molecule having at one terminal an atomic group capable of reaction with a thiol group or a carboxylic group.

A DNA probe having an amino group or a thiol group imparted to the 5' terminal of DNA in the synthesizing step can be used as the DNA probe 10 in step S5. The amino group or thiol group can be imparted easily by using a kit used exclusively for a DNA synthesizer available on the market. A base sequence that can be hybridized with an optional sequence significant in genetics, biochemistry, immunology or pathology can be used in the DNA probe 10, and any sequence can be selected.

The treating conditions in the process of each of steps S1, S2, S3, S4 and D5 relative to the inner wall 5 of the capillary 4 can be determined appropriately depending on the material, shape and size of the capillary used or on the kid of the DNA probe.

For performing the measurement by using the prepared DNA capillary, the processing liquid such as a sample, a reagent, etc. is injected into and discharged from the DNA capillary through the injecting open portion 2a and the discharging open portion 2b. A desired reaction time can be obtained by variously changing the discharge time from the discharging open portion 2b. For example, a sample is introduced through one opening of the capillary 4 so as to carry out reaction at temperatures lower by 10 to 15° C. than the melting point (Tm value) of DNA. Then, the capillary is washed with a washing liquid, followed by applying fluorimetry to the sample. A washing liquid having the stringency adjusted by changing appropriately the temperature for use and the composition should desirably be used as the washing liquid. Where the process involved in the measurement of the sample includes a hybridization reaction with the immobilized DNA, the DNA in the sample is made ready for hybridization and, then, is applied to the DNA capillary. Where the biological material itself to be measured is liquid, the biological material can be used as a sample to be measured. Also, a liquid material prepared by dissolving or dispersing the biological material to be measured in a suitable solvent can also be used as a sample to be measured. In short, liquid in an optional state can be used as a sample.

A single capillary is used in Example 1. However, a plurality of capillaries arranged in parallel or bundled together can be processed simultaneously. The plural capillaries, which can be arranged optionally, should desirably be arranged to make the arrangement convenient for a part or entire process involved in the measurement.

In Example 1, a photochemical reaction is performed once for immobilizing the DNA probe. However, it is possible to carry out photochemical reactions a desired number of times, as desired, so as to form DNA probes in the capillary.

EXAMPLE 2

FIGS. 4A and 4B show a DNA capillary according to a second embodiment of the present invention. The type shown in FIGS. 4A and 4B is adapted for efficiently manufacturing a plurality of DNA capillaries. To be more specific, a plurality of fluid passageways can be prepared at once and DNA probes can be immobilized simultaneously on the plural fluid passageways. The DNA capillary in Example 2 is called a DNA capillary array 24 for convenience.

FIG. 4A shows the entire system, and FIG. 4B is a plan view of the DNA capillary system 24. The body of the DNA capillary system 24 comprises a substrate 16 consisting of a lower substrate 16a and an upper substrate 16b bonded to the lower substrate 16a. Each of these lower and upper substrates 16a and 16b is made of glass, silicone, etc. A groove of the pattern as shown in the drawing is formed on the lower substrate 16a. A plurality of DNA capillaries 13a, 13b, 13c, etc. are formed by the groove. A groove of the pattern similar to that of the lower substrate 16a may also be formed on the upper substrate 16b, too. As shown in FIG. 4B, the ends at one side of the DNA capillaries 13a, 13b, 13c, etc. are positioned right under individual inlet-outlet ports 14a, 14b, 14c, etc. so as to be open to the outer air through the individual inlet-outlet ports 14a, 14b, 14c, etc. These DNA capillaries 13a, 13b, 13c, etc. are combined at the other ends to form a combined fluid passageway 17 extending to reach a region right under a common inlet-outlet port 15 and, thus, are open to the outer air through the common inlet-outlet port 15. These individual inlet-outlet ports 14a, 14b, 14c, etc. and the common inlet-outlet port 15 can be formed by forming thin adhesive layers at predetermined positions by utilizing, for example, a screen printing technology, followed by bonding tubular members such as glass tubes to the adhesive layers. DNA probes 12a, 12b, 12c, etc. are arranged in annular probe regions separated from each other and formed in the fluid passageways of the DNA capillaries 13a, 13b, 13c, etc., as shown in the drawing.

The method employing the photochemical reaction as in Example 1 can also be employed for immobilizing the DNA probes. Example 2 is effective in that a plurality of capillaries can be processed simultaneously. To be more specific, an immobilizing process solution used for immobilizing the DNA probes can be supplied from the common inlet-outlet port 15 to permit the process solution to flow through the combined fluid passageway 17 into the plural DNA capillaries simultaneously. Also, the process solution within the plural DNA capillaries can be discharged simultaneously from the common inlet-outlet ports 15.

Also, the light exposing process for allowing ultraviolet light to decompose the capping agent can be applied simultaneously to the plural capillaries. Specifically, a suitable ultraviolet light irradiating means is arranged above the DNA capillaries. Preferably, the ultraviolet light irradiating means should be of scanning type having a scanning length covering all the plural capillaries and capable of linearly irradiating all the capillaries with ultraviolet light. By moving freely the ultraviolet light irradiating means in an X-direction, i.e., a direction parallel to the fluid passageway in which the DNA probe is immobilized, and/or a Y-direction, i.e., a direction perpendicular to the fluid passageway, so as to scan the DNA capillaries 13a, 13b, 13c, etc., these DNA capillaries are linearly irradiated with ultraviolet light. By this process, the predetermined positions of all the DNA capillaries 13a, 13b, 13c, etc. are linearly irradiated with ultraviolet light. After removal of the capping agent by the irradiation, the further steps described in Example 1 are followed so as to immobilize the DNA probe 12a. In Example 2, it is not absolutely necessary for the lower substrate 16a to transmit light. If at least the upper substrate 16b transmits light, the wall surface in a desired position of fluid passageway formed by the lower substrate 16a and the upper substrate 16b is exposed to light in an annular shape so as to permit the DNA probe to be immobilized in an annular shape conforming with the shape of the light exposure. Then, similar scanning irradiation and immobilization of the DNA probe 12b are performed at a position to which the irradiating means is moved by a predetermined distance in the X-direction parallel to the DNA capillaries 13a, 13b, 13c, etc. so as to immobilize a second kind of DNA probe. The particular operation is repeated so as to form a plurality of DNA regions 12a, 12b, 12c, etc. arranged independent of each other, as shown in FIGS. 4A and 4B.

Where there is a DNA capillary the light exposure of which is desired to be avoided in the locus of scanning in the light exposure process, the light exposure of the particular DNA capillary can be avoided by, for example, selectively switching the irradiation by the ultraviolet light irradiation means by using a suitable switching circuit. In other words, some of the DNA capillaries can be selectively prevented from being irradiated with ultraviolet light in the scanning step. Therefore, it is possible to immobilize DNA probes of different combination for each of the DNA capillaries, leading to diversification of items to be measured. This is advantageous in that it is possible to perform measurement of only the minimum items required in the cases where many items are measured for a single sample and where different items are measured for a plurality of samples. In addition, since unnecessary DNA probes need not be immobilized in the step of preparing the DNA capillaries, the material can be utilized efficiently. It should also be noted that, if DNA probes of the same combination are immobilized in all the DNA capillaries 13, the same measurement can be performed simultaneously on samples the number of which is equal to the maximum number of capillaries.

As described previously, the immobilizing process liquid is introduced through the common inlet-outlet port 15 into the DNA capillaries 13a, 13b, 13c, etc. in the immobilizing process. It is desirable to discharge, particularly, the process liquid containing a DNA probe (see step S5 shown in FIG. 3) and the washing liquid used in the subsequent step through the individual inlet-outlet ports 14a, 14b, 14c, etc. independently. In this case, it is possible to avoid substantially completely the influences of contamination taking place in the case of using a plurality of different kinds of liquid. Also, it is desirable to inject sample liquids, etc. from the individual inlet-outlet ports 14a, 14b, 14c, etc. in measuring the samples. In this case, each liquid can be fluidized in a completely separated state from another liquid, leading to an improved measuring accuracy.

The DNA capillary 13 can be prepared in various sizes depending on the use. In practice, it may suffice for the DNA capillary to have a width of about 10 $\mu$m to 5 mm, a depth of about 1 $\mu$m to 500 $\mu$m, a length of about 5 mm to 100 mm, and a distance between adjacent DNA capillaries of about 10

μm to 5 mm. In general, however, the DNA capillary should desirably have a flattened structure in cross sectional shape having a large width and a small depth in view of the efficiency of reaction because the diffusion rate of cDNA converted from mRNA is low, i.e., about 5 μm/sec. The particular cross sectional shape of the DNA capillary is expected to shorten the reaction time, to diminish the amount of a sample used, and to increase the view field in the observing step.

The groove portion of the DNA capillaries 13a, 13b, 13c, etc. can be formed by various methods such as an excimer laser etching and an etching by photolithography. As an example, a groove forming method using a semiconductor processing technology will now be described with reference to the scheme shown in FIGS. 5A to 5H.

In the first step, an oxide film 19 is formed in a thickness of about b 5000Å on a silicon wafer substrate 20, followed by forming a resist film 18 on the oxide film 19, as shown in FIG. 5A. Then, a mask conforming with a groove pattern on the silicon wafer substrate 20 is prepared, followed by exposing selectively the resist film 18 to light by using an aligner so as to develop the groove pattern, as shown in FIG. 5B. The patterned resist film is used in the next step for etching the oxide film 19, as shown in FIG. 5C. The etching is performed by using an etchant consisting of hydrofluoric acid and ammonium fluoride mixed at a mixing ratio of about 1:9.

Then, the resist film 18 is removed by a method using a mixed solution consisting of sulfuric acid and hydrogen peroxide solution or using an oxygen plasma. After removal of the resist film 18, the silicon wafer substrate 20 is etched by using the patterned oxide film 19, as shown in FIG. 5E. Various known etching methods can be employed in this step including an isotropic or anisotropic wet etching and a dry etching using plasma gas. After the etching of the substrate 20, the oxide film 19 is removed, as shown in FIG. 5F. Since the oxide film 19 is simply removed, it is possible to use in this step a dilute solution, e.g., 50% solution, prepared by diluting, for example, a hydrofluoric acid solution with pure water. Finally, the entire silicon wafer substrate 20 including the groove portion is covered with a silicon oxide film 21, as shown in FIG. 5G.

After the physical processing of the groove as described above, a lid 23 which transmits light is bonded as shown in FIG. 5H so as to prepare the DNA capillary array, in which the individual inlet-outlet ports 14a, 14b, 14c, etc. and the common inlet-outlet port 15 are formed as shown in FIGS. 4A and 4B. The substrate 16 shown in FIG. 4A corresponds to the silicon wafer substrate 20 covered with the oxide film 21 and the lid 23. An anodic bonding method can be employed for the bonding of the lid 23. The anodic bonding method referred to above represents a bonding method in which a voltage of 1,000V is applied between the silicon wafer substrate 20 and the lid 23 while heating the substrate to about 500° C. For employing the anodic bonding method, it is necessary to use the lid 23 made of, for example, pyrex having the thermal expansion coefficient substantially equal to that of silicon. The silane treatment may be performed either before or after the bonding between the silicon wafer substrate 20 and the lid 23. It is not absolutely necessary to apply a silane treatment to the lid 23. However, it is desirable to apply a silane treatment to the lid 23. The silane treatment applied to the lid 23 may be performed either before or after the bonding of the lid 23 to the substrate 20. Where the silane treatment is applied to the lid 23, the DNA probes can be immobilized annularly as shown in FIGS. 4A and 4B, making the silane treatment advantageous in the immobilizing efficiency and the reaction sensitivity. On the other hand, where the silane treatment is not applied to the lid 23, the DNA probes are immobilized by the photochemical reaction in only the groove portion of the silicon wafer substrate 20 so as to obtain U-shaped probe regions. Even in this case, the resultant structure can be used as a DNA capillary array of the present invention.

The silicon wafer substrate 20 is used in the groove formation described above. However, a glass substrate such as a quartz substrate or a pyrex substrate can be used in place of the silicon substrate. In this case, a metal mask such as a gold mask is used in place of the oxide film 19 for the etching of the substrate. Also, the anodic bonding method can be employed for the bonding of the lid 23 to the substrate 20, if a silicon thin film is formed between the substrate 20 and the lid 23. Further, the oxide film 19 used as the etching mask of the silicon wafer substrate 20 can be replaced by, for example, a silicon nitride film or an alumina film.

The DNA capillary array 24 thus prepared produces prominent function and effect as described below. Specifically, since quantities of DNA capillaries can be prepared at once, the manufacturing cost can be lowered. Also, the DNA capillaries can be handled easily. It should also be noted that, since deprotection can be performed in an annular form by irradiating the fluid passageway formed of the capillary with an ultraviolet light, the DNA probe can be efficiently immobilized in an annular form on the inner wall of the capillary so as to improve the measuring sensitivity of the sample. Also, since a plurality of DNA capillaries are formed as an integral structure, the DNA capillary array 24 is advantageous in measuring many samples. For example, different samples can be introduced through the individual inlet-outlet ports 14a, 14b, 14c, etc. and, after biological reactions by incubation for a predetermined time, the samples can be collectively recovered from the common inlet-outlet port 15. Further, the washing liquid and the reagent for measurement can be similarly processed, thereby facilitating the automation and providing an apparatus having a high measurement processing capability.

The DNA capillary of the present invention is not limited to the Examples described above and can be modified in various fashions. For instance, in each of the Examples described above, the injection and discharge of the liquid sample, etc. are performed through different open portions, with the result that each liquid flows in one direction without fail. However, it is possible to allow the liquid to be discharged through the open portion through which the liquid was introduced previously such that the discharge direction is opposite to the injecting direction. Also, in Example 1, a discharge means such as a pipette is used for injecting a liquid for the immobilizing treatment and a liquid for measurement of a sample into the capillary 4. However, other methods can also be employed. For example, a natural injection by capillary force can be achieved by simply dipping the tip portion (injecting open end portion 2a) of the capillary 4 directly in a container containing a required amount of a liquid for the immobilizing treatment or a liquid for the sample measurement. Likewise, a natural discharge can be achieved without using a special sucking device by simply bringing the tip portion (discharging open portion 2b) into contact with a material readily absorbing water such as sponge or a water-absorbing polymer. Therefore, the DNA capillary can be handled easily either manually or automatically. Also, the capillary 4 in Example 1 produces the similar function and effect even if the capillary 4 is used under the state of lying lateral or erected upright. Where the capillary 4 is erected upright such that the injecting open portion 2a occupies the upper portion, the liquid injection can be performed through the upper injecting open portion 2a while discharging the liquid through the lower discharging open portion 2b, and vice versa.

In Example 2, the DNA capillaries 13a, 13b, 13c, etc. arranged in parallel are joined at one side to the combined fluid passageway 17. However, it is also possible to arrange radially these DNA capillaries 13a, 13b, 13c, etc. such that one end portions of these DNA capillaries are joined together at the common inlet-outlet port 15 positioned in the central portion, with the other end portions arranged on a single circular line. Also, if the plural DNA capillaries 13a, 13b, 13c, etc. are arranged to form independent fluid passageways in place of being joined together in the combined fluid passageway 17, it is possible to provide an integrated array which permits processing a plurality of samples efficiently.

The DNA capillary of the present invention can also be used for isolation and purification of DNA or mRNA in addition to the measurement of samples. Also, a protein involved in the antigen-antibody reaction can be used as the probe immobilized in the DNA capillary of the present invention. Further, in measuring the sample, the DNA probe can be selected appropriately from among known DNA probes using optical reaction principles. Also, various reagents required for the measurement such as marker reagents including a fluorescent material, a chemical light-emitting material and a color developing material can be utilized in accordance with the known chemical analytical technology. If necessary, an analytical apparatus available on the market, which is adapted for the selected reaction principle, can be used for automatic measurement.

As described above, the DNA capillary itself forms a fluid passageway in the present invention, making it possible to carry out easily various reactions such as immobilization, measurement and isolation as well as the washing operation. Also, if the DNA capillary of the present invention is connected to a liquid processing apparatus for consecutively processing various liquids, a series of operations can be performed easily. Also, in the case of using a DNA probe in which optional base sequences are synthesized in advance over the entire length of the base sequence, the DNA probe can be immobilized in a single light irradiation, making it possible to markedly suppress the damage done to the DNA probe. It follows that a satisfactory immobilized state can be maintained. Further, since a plurality of kinds of DNA probes are arranged in annular probe regions separately from each other along the fluid passageway, the plural DNA probes can be subjected to a coupling reaction simultaneously and efficiently by simply introducing the sample into the fluid passageway. Still further, since the surface having the DNA probe immobilized thereon is protected inside the capillary, the contamination problem can be eliminated substantially completely. In addition, the DNA capillary can be handled easily.

In Example 2, an optional DNA probe is immobilized in the capillary by a single photochemical reaction, as in Example 1. However, the photochemical reaction can be performed an optional number of times, as desired, so as to prepare a DNA probe having a desired base sequence.

EXAMPLE 3

FIGS. 6A to 6E collectively show a DNA capillary according to a third embodiment of the present invention. The numerals shown in these drawings exemplify desired sizes (mm). Of course, the sizes are not limited to those shown in the drawings. FIG. 6C is a cross sectional view along the line A—A shown in FIG. 6B. FIG. 6D is a cross sectional view along the line B—B shown in FIG. 6B. Further, FIG. 6E shows in a magnified fashion portions C and D shown in FIG. 6B. This embodiment is directed to a DNA capillary array 30 comprising a substrate 31 and a plurality of fluid passageways 32 formed in the substrate 31, as shown in FIG. 6B. Each fluid passageway 32 has open end portions 33 and is uniform in depth over the entire length. On the other hand, the width of each fluid passageway 32 is gradually diminished from the position right under the open portion 33 toward the center of the fluid passageway within the region ahead of the processing region including the probe region and is rendered constant within the processing region as shown in FIG. 6E. The cross sectional area of the processing region is constant over the entire region of the processing region. Each open portion 33 is deviated from the open portions of the adjacent fluid passageways in a direction perpendicular to the fluid flowing direction. In order to arrange the fluid passageways of the particular construction in a high density, the adjacent fluid passageways are arranged such that the tips of the fluid passageways are deviated from each other in the fluid flowing direction as shown in FIG. 6B.

As shown in FIGS. 6A and 6B, the processing regions 34, when cut along a plane perpendicular to the flowing direction, are arranged in the same position in all the fluid passageways. In other words, all the processing regions 34 have the same length in the longitudinal direction and are arranged such that the both ends of these processing regions 34 are aligned. In other words, the both ends of these processing regions are aligned on straight lines each perpendicular to the fluid flowing direction. In FIG. 6B, the processing regions are denoted by a reference numeral 34 and the straight lines noted above are denoted by broken lines. The particular arrangement is convenient for the probe immobilization and for the detecting operation. Particularly, it is possible to carry out a linear processing for the probe immobilization and the detection. Also, the reaction can be carried out under predetermined conditions for a plurality of fluid passageways.

Also, as shown in FIG. 6B, the particular arrangement of the present invention permits ensuring a sufficient distance between each open portion 33 and each of the open portions 33 of the first adjacent fluid passageways and a sufficient distance between each open portion 33 and each of the open portions 33 of the fluid passageways positioned adjacent to the first adjacent fluid passageways. As a result, it is possible to prevent the other open portions 33 from being contaminated even if a liquid splashing or liquid leakage takes place in the step of adding a liquid to a target open portion 33 by using, for example, a pipet. The distance between each open portion 33 and the adjacent open portion 33 is longer than the distance between each processing region 34 and the adjacent processing region 34. In other words, the pitch of between the adjacent open portions 33 is longer than the pitch between the adjacent process regions 34.

As apparent from FIG. 6C, the open portion 33 forms a cylindrical passageway extending from the distal end of the fluid passageway 32 in the vertical direction. In order to promote the inflow and outflow of the liquid into and out of the fluid passageway 32, the cross sectional area of the open portion 33 along a plane perpendicular to the fluid flowing direction is larger than the cross sectional area of the fluid passageway 32. It is possible to change the volume of the cylindrical open portion 33 in view of the liquid amount housed in the fluid passageway 32 in order to permit the inflow and outflow of the liquid to be performed smoothly. The open portion 33 in Example 3, which is shown in FIGS. 6A to 6E, is formed in the shape of a cylinder having a diameter of 6 mm and has a depth 2.0 mm. Since each fluid passageway 32 communicates with two open portions 33, it is possible to house a sufficient amount of liquid, e.g., 50 to 120 µL of liquid, in the fluid passageway 32. Particularly, since the fluid passageway 32 forms a slender capillary in which the fluid flow rate is relatively low, it is possible to handle the liquid more efficiently by pooling the liquid within the open portion 33 such that the pooled liquid is introduced into the fluid passageway or taken out. In other words, the open portion 33 also performs the function of a liquid reservoir in this embodiment. It is also possible to use the open portion 33 as a joining section for joining an injection-ejection means such as a pump or a pipet to the capillary array.

The tapered portion of the fluid passageway 32 serves to moderate the impact in the injecting step of the liquid. Also, it is possible for the tapered portion noted above to prevent relatively large bubbles among the bubbles that may be mixed into the liquid from entering the fluid passageway 32. It follows that the inflow of the fluid can be performed easily in the step of the manual injection or the automatic injection performed at a high speed.

As shown in FIG. 6D, according to this embodiment, the cross section of the fluid passageway along a plane crossing the fluid flowing direction is shaped rectangular with two roundish corners.

It is advantageous for the cross section of the groove to be shaped arcuate. This type is advantageous in that the capillary array can be manufactured easily, that it is possible to prevent significantly the micro bubbles mixed in the liquid from being attached to the corner portions of the fluid passageway, and that it is possible to prevent new bubbles from being generated and to prevent the bubbles from staying in the fluid passageway.

The DNA capillary according to this embodiment can be manufactured by injection molding of a plastic material. To be more specific, the DNA capillary can be prepared by bonding a flat substrate 31b to a substrate 31a having the fluid passageways 32 and open end portions 33 formed therein, said fluid passageways being formed by shaving and molding. The DNA probes are immobilized to the DNA regions arranged as described below by means of spotting. The DNA regions are linearly arranged on the flat substrate 31b in a direction perpendicular to the fluid flowing direction such that the adjacent DNA regions are parallel to each other.

It is possible to manufacture the DNA array of Example 3 by the method described in Example 2. It is also possible to change as desired the number of fluid passageways formed in the DNA capillary array for Example 3.

It is not absolutely necessary in the present invention to form the tapered portion in the fluid passageway. It suffices to form the tapered portion as desired in a desired shape.

EXAMPLE 4

Example 4 is directed to a DNA capillary, in which the open portion is arranged on the side surface of the DNA capillary, a taper 40 is arranged only on the side of the fluid passageway, and a probe region 42 is arranged on the flat bottom surface of the fluid passageway, as shown in FIG. 7. The probe region 42 is arranged on the flat bottom surface of a fluid passageway having a roundish rectangular cross sectional shape. The DNA capillary as shown in FIG. 7 can be manufactured by a method similar to the method described previously in conjunction with Example 3. Use of the flat bottom surface permits facilitating the immobilization of the probes, the detection of the signals, and the manufacture of the DNA capillary array.

EXAMPLE 5

Figure 8:
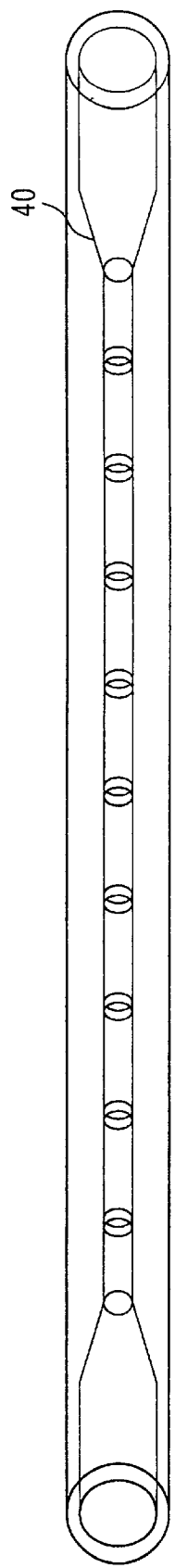
FIG. 8 is an oblique view showing the DNA capillary for Example 5.

Example 5 is directed to a DNA capillary comprising open portions having tapered portions 40 formed in the end portions of a fluid passageway, and a single fluid passageway, as shown in FIG. 8. The DNA capillary in this Example can be manually handled. In manually handling the DNA capillary, it is possible to inject a liquid into the fluid passageway through one of the two open portions by using, for example, a pipet. It is also possible to mount projections to the DNA capillary or to make elliptical the fluid passageway and/or the open portion so as to inhibit rolling of the DNA capillary.

EXAMPLE 6

Figure 9:
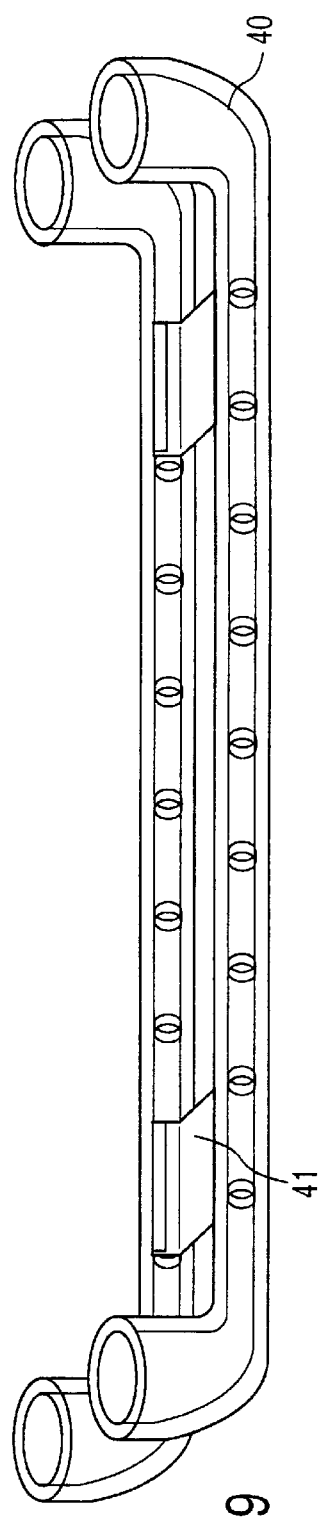
FIG. 9 is an oblique view showing the DNA capillary array for Example 6.

Example 6 is directed to a DNA capillary array comprising two cylindrical DNA capillaries and a joining member 41 for joining these two capillaries, as shown in FIG. 9. All the open portions of each capillary are bent upward. It is possible to form a tapered portion 40 in that portion of the fluid passageway which is positioned upward of the bent portion so as to allow the tapered portion to perform the function of the open portion described previously in conjunction with Example 3. It is possible to manufacture the particular capillary array by forming two parts of each capillary, which are divided from each other at the bent portion of each capillary, and bonding these two parts. It is also possible to manufacture the capillary array by the conventional technique depending on the material used.

The DNA capillary provided by the present invention differs from the conventional DNA capillary in that the immobilization of DNA, measurement, etc. can be performed within a closed system, with the result that the DNA capillary of the present invention is strong against contamination and can be handled easily. Also, since a capillary force is utilized in the present invention, the fluid required for the various processing such as various liquids including, for example, a sample and washing liquid, can be handled easily in performing the measurement by utilizing the immobilized DNA probe. Further, if a combined passageway is joined to a plurality of fluid passageways, various processing liquids can be collectively introduced into or recovered from the capillaries through the combined passageway, leading to an increased processing capacity. Still further, the immobilized area within the annular passageway can be increased by applying a photochemical reaction to the light-transmitting fluid passageway, making it possible to perform measurement, etc. efficiently even in the case of using traces of samples. In addition, since a plurality of different DNA probes are immobilized in a single fluid passageway, the measurement can be performed further efficiently. What should also be noted is that a DNA probe having at least 20 bases can be immobilized stably by immobilizing a DNA probe, in which a desired base sequence is synthesized in advance, by a single photoreaction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A DNA capillary comprising:

at least one tubular fluid passageway for a liquid defined by a wall for transmitting light in at least a part thereof, said tubular fluid passageway extending straight on the substrate in a longitudinal direction, the cross sectional area of said tubular fluid passageway along a plane perpendicular to a fluid flowing direction being constant over the entire length of a processing region of said tubular fluid passageway, the processing region of said tubular fluid passageway producing a capillary function, said tubular fluid passageway being bent and tapered at least partially to prevent bubble generation in the liquid; and a plurality of different kinds of DNA probes formed in an inner wall of said tubular fluid passageway, said DNA probes being immobilized in a ring-like manner to make one complete rotation along the inner wall of said tubular fluid passageway in a predetermined amount for each kind of DNA probe and independently from each other depending on the kind of DNA probe.

2. The DNA capillary according to claim 1, wherein said capillary has a plurality of said tubular fluid passageways and said tubular fluid passageways are integrally arranged.

3. The DNA capillary according to claim 1, wherein said DNA probes are immobilized by a photochemical reaction, and wherein a capping agent which is subjected to photodecomposition under irradiation with light having a predetermined wavelength is coupled with all amino groups present on the surface of the inner wall of said tubular fluid passageway.

4. The DNA capillary according to claim 1, wherein said DNA capillary has a plurality of said tubular fluid passageways, said tubular fluid passageways are integrally arranged, and said DNA probe is immobilized by a photochemical reaction.

5. The DNA capillary according to claim 1, wherein said DNA capillary has a plurality of said tubular fluid passageways, said tubular fluid passageways are integrally arranged, and all of said tubular fluid passageways communicate with a combined fluid passageway in at least distal end portions on one side.

6. The DNA capillary according to claim 1, wherein said DNA probes comprise at least 20 base sequences before the DNA probes are immobilized, and the DNA probes are immobilized in said probe regions by a single photochemical reaction.

7. The DNA capillary according to claim 1, wherein said DNA probe comprises at least 20 bases.

8. The DNA capillary according to claim 1, wherein the cross sectional shape of the tubular fluid passageway includes a curved portion.

9. The DNA capillary according to claim 1, wherein the tubular fluid passageway has a rectangular cross sectional shape having roundish corner portions.

10. The DNA capillary according to claim 1, wherein the probe regions are arranged separately from each other along the tubular fluid passageway.

11. The DNA capillary according to claim 1, wherein said probe regions are arranged about 1 μm to 5 mm apart from each other.

12. The DNA capillary according to claim 1, wherein the DNA capillary has an inner diameter of about 0.1 mm to about 5 mm and a length of about 5 mm to about 100 mm.

13. The DNA capillary according to claim 12, wherein the DNA capillary has an inner diameter of 0.5 mm to 1 mm.

14. A DNA capillary comprising:

a plurality of tubular fluid passageways for a liquid defined by a wall for transmitting light in at least a part thereof, said tubular fluid passageway extending straight on the substrate in a longitudinal direction, the cross sectional area of said tubular fluid passageway along a plane perpendicular to a fluid flowing direction being constant over the entire length of a processing region of said tubular fluid passageway, the processing region of said tubular fluid passageway producing a capillary function, wherein adjacent open portions are arranged deviant from each other in the fluid flowing direction, and the processing regions of all the tubular fluid passageways are equal to each other in length in the fluid flowing direction and both ends of the processing regions are aligned; and a plurality of different kinds of DNA probes formed in an inner wall of said tubular fluid passageway, said DNA probes being immobilized in a ring-like manner to make one complete rotation along the inner wall of said tubular fluid passageway in a predetermined amount for each kind of DNA probe and independently from each other depending on the kind of DNA probe.

15. The DNA capillary of claim 14, wherein said tubular fluid passageways are bent and tapered at least partially to prevent bubble generation in the liquid.

16. The DNA capillary according to claim 14, wherein said tubular fluid passageways are integrally arranged.

17. The DNA capillary according to claim 14, wherein said DNA probes are immobilized by a photochemical reaction, and wherein a capping agent which is subjected to photodecomposition under irradiation with light having a predetermined wavelength is coupled with all amino groups present on the surface of the inner wall of said tubular fluid passageways.

18. The DNA capillary according to claim 14, wherein said tubular fluid passageways are integrally arranged, and said DNA probe is immobilized by a photochemical reaction.

19. The DNA capillary according to claim 14, wherein said tubular fluid passageways are integrally arranged, and all of said tubular fluid passageways communicate with a combined fluid passageway in at least distal end portions on one side.

20. The DNA capillary according to claim 14, wherein said DNA probes comprise at least 20 base sequences before the DNA probes are immobilized, and the DNA probes are immobilized in said probe regions by a single photochemical reaction.

21. The DNA capillary according to claim 14, wherein said DNA probe comprises at least 20 bases.

22. The DNA capillary according to claim 14, wherein the cross sectional shape of the tubular fluid passageways includes a curved portion.

23. The DNA capillary according to claim 14, wherein the tubular fluid passageways have a rectangular cross sectional shape having roundish corner portions.

24. The DNA capillary according to claim 14, wherein the probe regions are arranged separately from each other along the tubular fluid passageways.

25. The DNA capillary according to claim 14, wherein said probe regions are arranged about 1 μm to 5 mm apart from each other.

26. The DNA capillary according to claim 14, wherein the DNA capillary has an inner diameter of about 0.1 mm to about 5 mm and a length of about 5 mm to about 100 mm.

27. The DNA capillary according to claim 26, wherein the DNA capillary has an inner diameter of 0.5 mm to 1 mm.

* * * * *